(12) United States Patent
Schoonmaker et al.

(10) Patent No.: US 9,844,635 B2
(45) Date of Patent: Dec. 19, 2017

(54) ADJUSTABLE HEIGHT NEEDLE INFUSION DEVICE

(71) Applicant: Becton, Dickinson and Company, Franklin Lakes, NJ (US)

(72) Inventors: Ryan Schoonmaker, San Marcos, CA (US); Cole Constantineau, Cambridge, MA (US); Michel Bruehwiler, Newton, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 568 days.

(21) Appl. No.: 14/323,791

(22) Filed: Jul. 3, 2014

(65) Prior Publication Data

US 2014/0324017 A1    Oct. 30, 2014

Related U.S. Application Data

(62) Division of application No. 13/303,055, filed on Nov. 22, 2011, now Pat. No. 8,795,230.

(Continued)

(51) Int. Cl.
*A61M 5/46* (2006.01)
*A61M 5/158* (2006.01)
(Continued)

(52) U.S. Cl.
CPC ............. *A61M 5/46* (2013.01); *A61M 5/158* (2013.01); *A61M 5/488* (2013.01); *A61M 2005/14252* (2013.01); *A61M 2005/14264* (2013.01); *A61M 2005/1581* (2013.01); *A61M 2005/1585* (2013.01); *A61M 2005/1586* (2013.01);
(Continued)

(58) Field of Classification Search
CPC .................. A61M 5/158; A61M 5/46; A61M 2005/1581; A61M 2005/1585; A61M 2005/14252; A61M 2005/1587; A61M 2005/14264; A61M 5/488; A61M 2005/3289; A61M 2005/1586
See application file for complete search history.

(56) References Cited

U.S. PATENT DOCUMENTS

| 3,572,336 A | 3/1971 | Hershberg |
| 3,857,382 A | 12/1974 | Williams, Jr. et al. |

(Continued)

FOREIGN PATENT DOCUMENTS

| EP | 0 980 687 | 2/2000 |
| JP | 2004537339 A | 12/2004 |

(Continued)

*Primary Examiner* — Theodore Stigell
(74) *Attorney, Agent, or Firm* — Dickinson Wright PLLC

(57) ABSTRACT

An infusion set has a retraction dial that can be removably assembled with the infusion set and access a threaded needle hub contained therein such that the dial can be used to advance or retract a needle hub and an inserted needle to a more precisely controlled insertion depth to deliver insulin or other medicament intradermally (i.e. to the upper 3 mm of skin surface). Position of the inserted needle can be maintained by providing a separated and isolated needle hub, main base and main hub of the infusion set that can isolate the inserted needle from external forces such that the needle can be maintained at a depth to deliver content to the upper 3 mm of skin surface during normal use.

12 Claims, 5 Drawing Sheets

Related U.S. Application Data

(60) Provisional application No. 61/344,971, filed on Nov. 30, 2010.

(51) Int. Cl.
    *A61M 5/142*       (2006.01)
    *A61M 5/48*        (2006.01)
    *A61M 5/32*        (2006.01)

(52) U.S. Cl.
    CPC ............... *A61M 2005/1587* (2013.01); *A61M 2005/3289* (2013.01)

(56) References Cited

U.S. PATENT DOCUMENTS

| | | |
|---|---|---|
| 3,918,355 A | 11/1975 | Weber |
| 3,963,380 A | 6/1976 | Thomas, Jr. et al. |
| 4,204,538 A | 5/1980 | Cannon |
| 4,231,368 A | 11/1980 | Becker |
| 4,490,141 A | 12/1984 | Lacko et al. |
| 4,685,902 A | 8/1987 | Edwards et al. |
| 4,723,947 A | 2/1988 | Konopka |
| 4,734,092 A | 3/1988 | Millerd |
| 4,755,173 A | 7/1988 | Konopka et al. |
| 5,176,662 A * | 1/1993 | Bartholomew ... A61M 25/0606 128/DIG. 26 |
| 5,226,899 A | 7/1993 | Lee et al. |
| 5,242,406 A | 9/1993 | Gross et al. |
| 5,257,980 A | 11/1993 | Van Antwerp et al. |
| 5,453,099 A | 9/1995 | Lee et al. |
| 5,522,803 A | 6/1996 | Teissen-Simony |
| 5,536,249 A | 7/1996 | Castellano et al. |
| 5,545,143 A | 8/1996 | Fischell |
| 5,545,152 A | 8/1996 | Funderburk et al. |
| 5,593,390 A | 1/1997 | Castellano et al. |
| 5,728,074 A | 3/1998 | Castellano et al. |
| 5,800,420 A | 9/1998 | Gross et al. |
| 5,820,602 A | 10/1998 | Kovelman et al. |
| 5,851,197 A | 12/1998 | Marano et al. |
| 5,858,001 A | 1/1999 | Tsals et al. |
| 5,858,005 A | 1/1999 | Kriesel |
| 5,925,021 A | 7/1999 | Castellano et al. |
| 5,957,895 A | 9/1999 | Sage et al. |
| 5,968,011 A | 10/1999 | Larsen et al. |
| 5,980,506 A | 11/1999 | Mathiasen |
| 6,017,328 A | 1/2000 | Fischell et al. |
| 6,056,718 A | 5/2000 | Funderburk et al. |
| 6,068,615 A | 5/2000 | Brown et al. |
| 6,074,369 A | 6/2000 | Sage et al. |
| 6,086,575 A | 7/2000 | Mejslov |
| 6,093,172 A | 7/2000 | Funderburk et al. |
| 6,110,148 A | 8/2000 | Brown et al. |
| 6,123,690 A | 9/2000 | Mejslov |
| 6,132,400 A | 10/2000 | Waldenburg |
| 6,175,752 B1 | 1/2001 | Say et al. |
| 6,206,134 B1 | 3/2001 | Stark et al. |
| 6,254,586 B1 | 7/2001 | Mann et al. |
| 6,272,364 B1 | 8/2001 | Kurnik |
| 6,275,717 B1 | 8/2001 | Gross et al. |
| 6,277,627 B1 | 8/2001 | Helllnga |
| 6,293,925 B1 | 9/2001 | Safabash et al. |
| 6,302,866 B1 | 10/2001 | Marggi |
| 6,352,523 B1 | 3/2002 | Brown et al. |
| 6,355,021 B1 | 3/2002 | Nielsen et al. |
| 6,391,005 B1 | 5/2002 | Lum et al. |
| 6,485,461 B1 | 11/2002 | Mason et al. |
| 6,520,938 B1 | 2/2003 | Funderburk et al. |
| 6,521,446 B2 | 2/2003 | Hellinga |
| 6,544,212 B2 | 4/2003 | Galley et al. |
| 6,546,269 B1 | 4/2003 | Kurnik |
| 6,551,276 B1 | 4/2003 | Mann et al. |
| 6,558,351 B1 | 5/2003 | Steil et al. |
| 6,565,509 B1 | 5/2003 | Say et al. |
| 6,576,430 B1 | 6/2003 | Hsieh et al. |
| 6,579,267 B2 | 6/2003 | Lynch et al. |
| 6,589,229 B1 | 7/2003 | Connelly et al. |
| 6,607,509 B2 | 8/2003 | Bobroff et al. |
| 6,613,017 B1 | 9/2003 | Mickley |
| 6,656,158 B2 | 12/2003 | Mahoney et al. |
| 6,656,159 B2 | 12/2003 | Flaherty |
| 6,669,669 B2 | 12/2003 | Flaherty et al. |
| 6,692,457 B2 | 2/2004 | Flaherty |
| 6,699,218 B2 | 3/2004 | Flaherty et al. |
| 6,706,159 B2 | 3/2004 | Moerman et al. |
| 6,723,072 B2 | 4/2004 | Flaherty et al. |
| 6,740,059 B2 | 5/2004 | Flaherty |
| 6,749,560 B1 | 6/2004 | Konstrorum et al. |
| 6,749,587 B2 | 6/2004 | Flaherty |
| 6,768,425 B2 | 7/2004 | Flaherty et al. |
| 6,830,558 B2 | 12/2004 | Flaherty et al. |
| 6,830,562 B2 | 12/2004 | Mogensen et al. |
| 6,840,922 B2 | 1/2005 | Nielsen et al. |
| 6,852,104 B2 | 2/2005 | Blomquist |
| 6,949,084 B2 | 9/2005 | Marggi et al. |
| 6,960,162 B2 | 11/2005 | Saadat et al. |
| 6,960,192 B1 | 11/2005 | Flaherty et al. |
| 6,977,180 B2 | 12/2005 | Hellinga et al. |
| 6,997,907 B2 | 2/2006 | Safabash et al. |
| 7,004,928 B2 | 2/2006 | Aceti et al. |
| 7,018,360 B2 | 3/2006 | Flaherty et al. |
| 7,029,455 B2 | 4/2006 | Flaherty |
| 7,052,251 B2 | 5/2006 | Nason et al. |
| 7,064,103 B2 | 6/2006 | Pitner et al. |
| 7,070,580 B2 | 7/2006 | Nielsen |
| 7,083,597 B2 | 8/2006 | Lynch et al. |
| 7,109,878 B2 | 9/2006 | Mann et al. |
| 7,128,727 B2 | 10/2006 | Flaherty et al. |
| 7,137,964 B2 | 11/2006 | Flaherty |
| 7,144,384 B2 | 12/2006 | Gorman et al. |
| 7,207,974 B2 | 4/2007 | Safabash et al. |
| 7,214,207 B2 | 5/2007 | Lynch et al. |
| 7,226,278 B2 | 6/2007 | Nason et al. |
| 7,303,543 B1 | 12/2007 | Maule et al. |
| 7,303,549 B2 | 12/2007 | Flaherty et al. |
| 7,310,544 B2 | 12/2007 | Brister et al. |
| 7,318,816 B2 | 1/2008 | Bobroff et al. |
| 7,329,239 B2 | 2/2008 | Safabash et al. |
| 7,354,420 B2 | 4/2008 | Steil et al. |
| 7,496,392 B2 | 2/2009 | Alarcon et al. |
| 7,713,258 B2 | 5/2010 | Adams et al. |
| 7,722,595 B2 | 5/2010 | Pettis et al. |
| 8,172,803 B2 | 5/2012 | Morrissey et al. |
| 8,221,359 B2 | 7/2012 | Kristensen et al. |
| 8,262,618 B2 | 9/2012 | Scheurer |
| 8,277,415 B2 | 10/2012 | Mounce et al. |
| 8,285,328 B2 | 10/2012 | Caffey et al. |
| 8,287,467 B2 | 10/2012 | List et al. |
| 8,287,516 B2 | 10/2012 | Kornerup et al. |
| 8,306,596 B2 | 11/2012 | Schurman et al. |
| 8,310,415 B2 | 11/2012 | McLaughlin et al. |
| 8,313,468 B2 | 11/2012 | Geipel et al. |
| 2002/0040208 A1 | 4/2002 | Flaherty et al. |
| 2003/0055380 A1 | 3/2003 | Flaherty |
| 2003/0109829 A1 | 6/2003 | Mogensen et al. |
| 2003/0176852 A1 | 9/2003 | Lynch et al. |
| 2003/0199823 A1 | 10/2003 | Bobroff et al. |
| 2004/0002682 A1 | 1/2004 | Kovelman et al. |
| 2004/0010207 A1 | 1/2004 | Flaherty et al. |
| 2004/0044306 A1 | 3/2004 | Lynch et al. |
| 2004/0059316 A1 | 3/2004 | Smedegaard |
| 2004/0078028 A1 | 4/2004 | Flaherty et al. |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0162521 A1 | 8/2004 | Bengtsson |
| 2004/0204673 A1 | 10/2004 | Flaherty |
| 2004/0204687 A1 | 10/2004 | Mogensen et al. |
| 2004/0220551 A1 | 11/2004 | Flaherty et al. |
| 2004/0235446 A1 | 11/2004 | Flaherty et al. |
| 2004/0260233 A1 | 12/2004 | Garibotte et al. |
| 2005/0021005 A1 | 1/2005 | Flaherty et al. |
| 2005/0022274 A1 | 1/2005 | Campbell et al. |

(56) References Cited

U.S. PATENT DOCUMENTS

| | | |
|---|---|---|
| 2005/0043687 A1 | 2/2005 | Mogensen et al. |
| 2005/0065760 A1 | 3/2005 | Murtfeldt et al. |
| 2005/0090784 A1 | 4/2005 | Nielsen et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0113761 A1 | 5/2005 | Faust et al. |
| 2005/0124936 A1 | 6/2005 | Mogensen et al. |
| 2005/0131345 A1 | 6/2005 | Miller |
| 2005/0171512 A1 | 8/2005 | Flaherty |
| 2005/0182366 A1 | 8/2005 | Vogt et al. |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | Dilanni et al. |
| 2005/0245799 A1 | 11/2005 | Brauker et al. |
| 2005/0273076 A1 | 12/2005 | Beasley et al. |
| 2005/0283144 A1 | 12/2005 | Shiono et al. |
| 2006/0001551 A1 | 1/2006 | Kraft et al. |
| 2006/0041229 A1 | 2/2006 | Garibotto et al. |
| 2006/0074381 A1 | 4/2006 | Malave et al. |
| 2006/0122577 A1 | 6/2006 | Poulsen et al. |
| 2006/0129090 A1 | 6/2006 | Moberg et al. |
| 2006/0135913 A1 | 6/2006 | Ethelfeld |
| 2006/0142698 A1 | 6/2006 | Ethelfeld |
| 2006/0173410 A1 | 8/2006 | Moberg et al. |
| 2006/0178633 A1 | 8/2006 | Garibotto et al. |
| 2006/0200073 A1 | 9/2006 | Radmer et al. |
| 2006/0263839 A1 | 11/2006 | Ward et al. |
| 2006/0264835 A1 | 11/2006 | Nielsen et al. |
| 2006/0282290 A1* | 12/2006 | Flaherty ............ A61M 5/14248 705/2 |
| 2007/0016149 A1 | 1/2007 | Hunn et al. |
| 2007/0021733 A1 | 1/2007 | Hansen et al. |
| 2007/0049865 A1 | 3/2007 | Radmer et al. |
| 2007/0073229 A1 | 3/2007 | Gorman et al. |
| 2007/0073559 A1 | 3/2007 | Stangel |
| 2007/0088244 A1 | 4/2007 | Miller et al. |
| 2007/0088271 A1 | 4/2007 | Richards |
| 2007/0093754 A1 | 4/2007 | Mogensen et al. |
| 2007/0118405 A1 | 5/2007 | Campbell et al. |
| 2007/0149925 A1 | 6/2007 | Edwards et al. |
| 2007/0191702 A1 | 8/2007 | Yodfat et al. |
| 2007/0219496 A1 | 9/2007 | Kamen et al. |
| 2008/0004515 A1 | 1/2008 | Jennewine |
| 2008/0021395 A1 | 1/2008 | Yodfat et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0051714 A1 | 2/2008 | Moberg et al. |
| 2008/0051716 A1 | 2/2008 | Stutz |
| 2008/0051718 A1 | 2/2008 | Kavazov et al. |
| 2008/0051727 A1 | 2/2008 | Moberg et al. |
| 2008/0051730 A1 | 2/2008 | Bikovsky |
| 2008/0051738 A1 | 2/2008 | Griffin |
| 2008/0051765 A1 | 2/2008 | Mounce |
| 2008/0097321 A1 | 4/2008 | Mounce et al. |
| 2008/0097326 A1 | 4/2008 | Moberg et al. |
| 2008/0097327 A1 | 4/2008 | Bente et al. |
| 2008/0097328 A1 | 4/2008 | Moberg et al. |
| 2008/0097375 A1 | 4/2008 | Bikovsky |
| 2008/0097381 A1 | 4/2008 | Moberg et al. |
| 2008/0103483 A1 | 5/2008 | Johnson et al. |
| 2008/0116647 A1 | 5/2008 | Anderson et al. |
| 2008/0119707 A1 | 5/2008 | Stafford |
| 2008/0132842 A1 | 6/2008 | Flaherty |
| 2008/0147041 A1 | 6/2008 | Kristensen |
| 2008/0160492 A1 | 7/2008 | Campbell et al. |
| 2008/0194924 A1 | 8/2008 | Valk et al. |
| 2008/0204077 A1 | 8/2008 | Huang |
| 2008/0215006 A1 | 9/2008 | Thorkild |
| 2008/0243051 A1 | 10/2008 | Destefano |
| 2008/0261255 A1 | 10/2008 | Tolosa et al. |
| 2008/0264261 A1 | 10/2008 | Kavazov et al. |
| 2008/0269680 A1 | 10/2008 | Ibranyan et al. |
| 2008/0269713 A1 | 10/2008 | Kavazov |
| 2008/0281297 A1 | 11/2008 | Pesach et al. |
| 2008/0294028 A1 | 11/2008 | Brown |
| 2008/0306434 A1 | 12/2008 | Dobbles et al. |
| 2008/0312608 A1 | 12/2008 | Christoffersen et al. |
| 2008/0319414 A1 | 12/2008 | Yodfat et al. |
| 2009/0005724 A1 | 1/2009 | Regittnig et al. |
| 2009/0005728 A1 | 1/2009 | Weinert et al. |
| 2009/0012472 A1 | 1/2009 | Ahm et al. |
| 2009/0062767 A1 | 3/2009 | Van Antwerp et al. |
| 2009/0076453 A1 | 3/2009 | Mejlhede et al. |
| 2009/0198191 A1 | 8/2009 | Chong et al. |
| 2009/0198215 A1 | 8/2009 | Chong et al. |
| 2009/0221971 A1 | 9/2009 | Mejlhede et al. |
| 2009/0240240 A1 | 9/2009 | Hines et al. |
| 2009/0254041 A1 | 10/2009 | Krag et al. |
| 2009/0281497 A1 | 11/2009 | Kamen et al. |
| 2009/0326457 A1 | 12/2009 | O'Connor |
| 2010/0049129 A1 | 2/2010 | Yokoi et al. |
| 2010/0137799 A1* | 6/2010 | Imai ...................... A61M 5/158 604/115 |
| 2010/0160902 A1 | 6/2010 | Aeschilimann et al. |
| 2010/0286714 A1 | 11/2010 | Gyrn et al. |
| 2010/0291588 A1 | 11/2010 | McDevitt et al. |
| 2010/0298830 A1 | 11/2010 | Browne et al. |
| 2011/0313357 A1* | 12/2011 | Skutnik ............. A61M 5/14248 604/151 |
| 2012/0136300 A1 | 5/2012 | Schoonmaker et al. |
| 2012/0253282 A1 | 10/2012 | Nagel et al. |
| 2012/0259185 A1 | 10/2012 | Yodfat et al. |
| 2012/0265034 A1 | 10/2012 | Wisniewski et al. |
| 2012/0277554 A1 | 11/2012 | Schurman et al. |
| 2012/0277667 A1 | 11/2012 | Yodat et al. |
| 2012/0277724 A1 | 11/2012 | Larsen et al. |
| 2012/0283540 A1 | 11/2012 | Brüggemann |
| 2012/0291778 A1 | 11/2012 | Nagel et al. |
| 2012/0293328 A1 | 11/2012 | Blomquist |
| 2012/0296269 A1 | 11/2012 | Blomquist |
| 2012/0296310 A1 | 11/2012 | Blomquist |
| 2012/0296311 A1 | 11/2012 | Brauker et al. |

FOREIGN PATENT DOCUMENTS

| | | | |
|---|---|---|---|
| JP | 2006341095 A | 12/2006 | |
| JP | 2007511325 A | 5/2007 | |
| JP | 2010501281 A | 1/2010 | |
| JP | 2010533525 A | 10/2010 | |
| WO | WO 99-34212 | 7/1999 | |
| WO | WO 2005/000382 A2 | 1/2005 | |
| WO | WO 2007-051139 | 5/2007 | |
| WO | WO 2008/024810 A2 | 2/2008 | |
| WO | 2008086552 A2 | 7/2008 | |
| WO | WO 2008/086552 A2 | 7/2008 | |
| WO | WO 2009/010399 A1 | 1/2009 | |
| WO | WO 2009010399 A1 * | 1/2009 | ............ A61M 5/158 |
| WO | WO 2009-021039 | 2/2009 | |
| WO | WO 2009-021052 | 2/2009 | |
| WO | WO 2010/080715 A1 | 7/2010 | |
| WO | WO 2011/051940 A1 | 5/2011 | |

* cited by examiner

ADJUSTABLE HEIGHT NEEDLE INFUSION DEVICE

CROSS-REFERENCE TO RELATED APPLICATIONS

This application is a division of a U.S. patent application of Ryan Schoonmaker et al. entitled "Adjustable Height Needle Infusion Device", Ser. No. 13/303,055, filed Nov. 22, 2011, which issued Aug. 5, 2014 as U.S. Pat. No. 8,795,230, and which claims the benefit under 35 U.S.C. §119(e) of a U.S. provisional patent application of Ryan Schoonmaker et al. entitled "Adjustable Height Needle Infusion Device", Ser. No. 61/344,971, filed on Nov. 30, 2010, the entire content of both of said prior applications being incorporated herein by reference.

FIELD OF THE INVENTION

The present invention relates generally to components and elements of infusion sets, including a retraction dial for an infusion set, which ensures proper positioning of needle insertion by removably coupling with an infusion set and allowing a user to adjust a final needle depth by turning the dial.

BACKGROUND OF THE INVENTION

A large number of people, including those suffering from conditions such as diabetes use some form of infusion therapy, such as daily insulin infusions to maintain close control of their glucose levels. There are two principal modes of daily insulin. therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients Who have used pumps prefer to remain with pumps for the rest of their lives. This is because infusion pumps, although more complex than syringes and pens, offer the advantages of continuous infusion of insulin, precision dosing and programmable delivery schedules. This results in closer blood glucose control and an improved feeling of wellness.

The use of an infusion pump requires the use of a disposable component, typically referred to as an infusion set or pump set, which conveys the insulin from a reservoir within the pump into the skin of the user. An infusion set typically consists of a pump connector, a length of tubing, and a hub or base from which an infusion needle or cannula extends. The hub or base has an adhesive which retains the base on the skin surface during use, and may be applied to the skin manually or with the aid of a manual or automatic insertion device.

Currently, most insulin infusion sets deliver insulin to the sub-cutaneous layers of skin using either fixed metal needles or flexible plastic cannulas. Such infusion sets typically deliver insulin 4-10 mm below the skin surface. However, the upper 3 mm of skin surface, the intradermal space, facilitates better drug absorption. Unfortunately, due to the, relative, thinness of the intradermal layer, inserting a needle at such depth and maintaining an infusion site over an extended period of time within this narrow band is difficult.

Further, most insulin infusion sets typically do not provide any features to isolate the inserted needle from shock or other external forces. Since these infusion sets typically deliver insulin 4-10 mm below the skin surface, shock or other external forces to the set have less effect on the deeper inserted needle. However, where an attempt is made to target the upper 3 mm of skin surface, any shock or movement of the set can adversely affect needle insertion and infusion performance.

Still further, most insulin sets have inserters that can result in skin surface "tenting" during needle insertion, where the skin surface is deflected somewhat prior to or during needle insertion, which makes precisely targeting the upper 3 mm of skin surface difficult.

Accordingly, a need exists for advanced, improved, and novel components and elements of current and future infusion sets that can deliver content to the upper 3 mm of skin surface, the intradermal space, to facilitate better drug absorption, while maintaining a degree of comfort to the user.

SUMMARY OF THE INVENTION

An object of the present invention is to provide an infusion set which can deliver insulin or other medicament to the upper 3 mm of skin surface, the intradermal space, to facilitate better drug absorption, while maintaining a degree of comfort to the user.

Another object of the present invention is to provide an infusion set having an inserter that can insert a needle which can be removed from the infusion set after insertion.

Another object of the present invention is to provide an infusion set with a removable retraction dial on its upper surface, wherein the retraction dial can be used to precisely retract an inserted needle to reach a desired depth to deliver insulin or other medicament to the upper 3 mm of skin surface, or retract an inserter needle some distance into a soft cannula after insertion.

Another object of the present invention is to provide an infusion set that includes a needle hub in a threaded engagement with a main base, such that rotation of the needle hub relative to the main base results in retraction or advancement of a needle of the needle hub.

Another object of the present invention is to provide an infusion set with the removable retraction dial to rotate the needle hub relative to the main base to precisely retract an inserted needle to reach a desired depth to deliver insulin or other medicament to the upper 3 mm of skin surface.

Another object of the present invention is to provide an infusion set that can isolate an inserted needle from external forces such that the needle can he maintained at a depth to deliver insulin or other medicament to the upper 3 mm of skin surface during normal use.

These and other objects are substantially achieved by providing an infusion set having a retraction dial that can be removably assembled with the infusion set and access a threaded needle hub contained therein such that the dial can be used to advance or retract an inserted needle to a depth to deliver insulin or other medicament to the upper 3 mm of skin surface, or retract an inserter needle some distance into a soft cannula after insertion. Position of the inserted needle can be maintained by providing a needle hub, main base and main hub of the infusion set that can isolate the inserted needle from external forces such that the needle can be maintained at a depth to deliver insulin or other medicament to the upper 3 mm of skin surface during normal use.

BRIEF DESCRIPTION OF THE DRAWINGS

The various objects, advantages and novel features of the exemplary embodiments of the present invention will be more readily appreciated from the following detailed description when read in conjunction with the appended drawings, in which.

Throughout the drawings, like reference numerals will be understood to refer to like parts, components and structures.

DETAILED DESCRIPTION OF THE EXEMPLARY EMBODIMENTS

Figure 1:
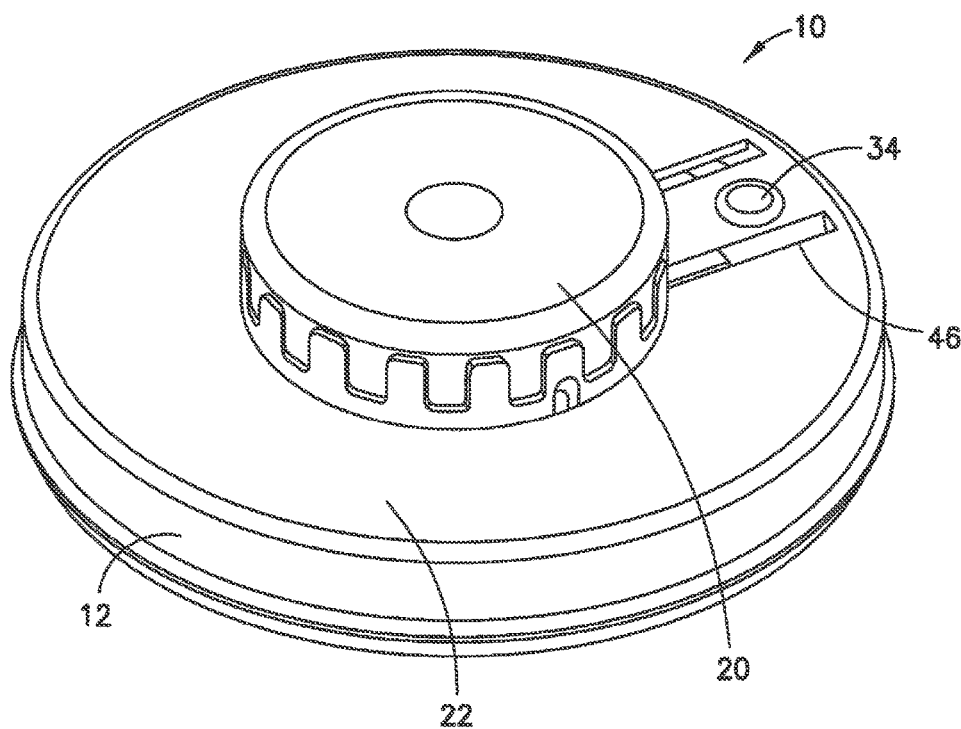
FIG. 1 is a perspective view of an infusion set in accordance with an embodiment of the present invention.

The exemplary embodiments of the present invention described below provide a novel means of delivering insulin to the intradermal layers of skin via a standard insulin pump. In particular, the exemplary embodiments of the present invention provide an infusion set with a retraction dial to advance or retract an inserted needle to deliver insulin to the upper 3 mm of skin surface, the intradermal space, to facilitate better drug absorption, while maintaining a degree of comfort to the user.

As will be appreciated by one skilled in the art, there are numerous ways of carrying out the examples, improvements and arrangements of insulin-associated devices disclosed herein. Although reference will be made to the exemplary embodiments depicted in the drawings and the following description, the embodiments disclosed herein are not meant to he exhaustive of the various alternative designs and embodiments that are encompassed by the disclosed invention.

As noted, the exemplary embodiments of the present invention deliver insulin to the intradermal layers of the skin via a standard insulin pump or other similar device. By utilizing a refraction dial, and an isolated needle hub, proper insertion and maintenance of the inserted needle in the intradermal space is ensured. Position of the inserted needle can be maintained by providing a needle hub, main base and main hub of the infusion set, and tube attachment, that can isolate the inserted needle from external forces such that the desired needle depth can be maintained.

Proper needle insertion stands as a primary obstacle to infusing insulin via a pump into the intradermal layer. In the exemplary embodiments of the present invention, the initial insertion of the needle is substantially the same as performed using any standard infusion set, but a removable retraction dial is provided to advance or retract the inserted needle, or retract an inserter needle some distance into a soft cannula after insertion. By retracting the inserted needle a slight distance, medicament can be delivered into the thin intradermal layer. Utilizing precision parts, this process can be reliable when compared to a standard manual intradermal injection procedure, such as the Mantoux technique.

However, maintaining the position of the needle within the intradermal layers of the skin over the course of a typical three-day period poses significant technical challenges. Accordingly, the exemplary embodiments of the present invention further provide at least two methods of anchoring the needle in place. First, the main base of the device creates and maintains a preload on the skin surface, which locks the needle in place vertically. Second, an adhesive may be applied to the main base in the area of the needle, locking the skin surface to the needle location.

Figure 2:
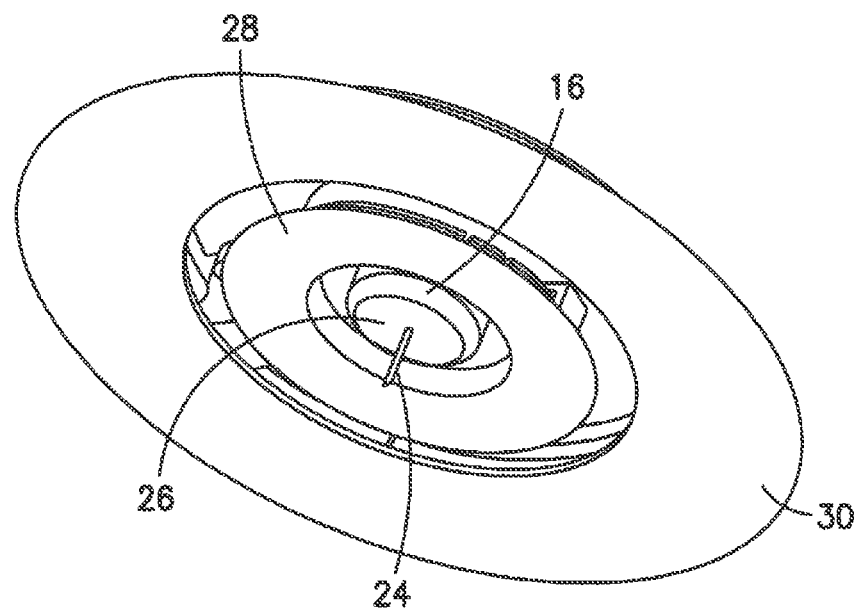
FIG. 2 is a bottom perspective view of the infusion set of FIG. 1.
Figure 3:
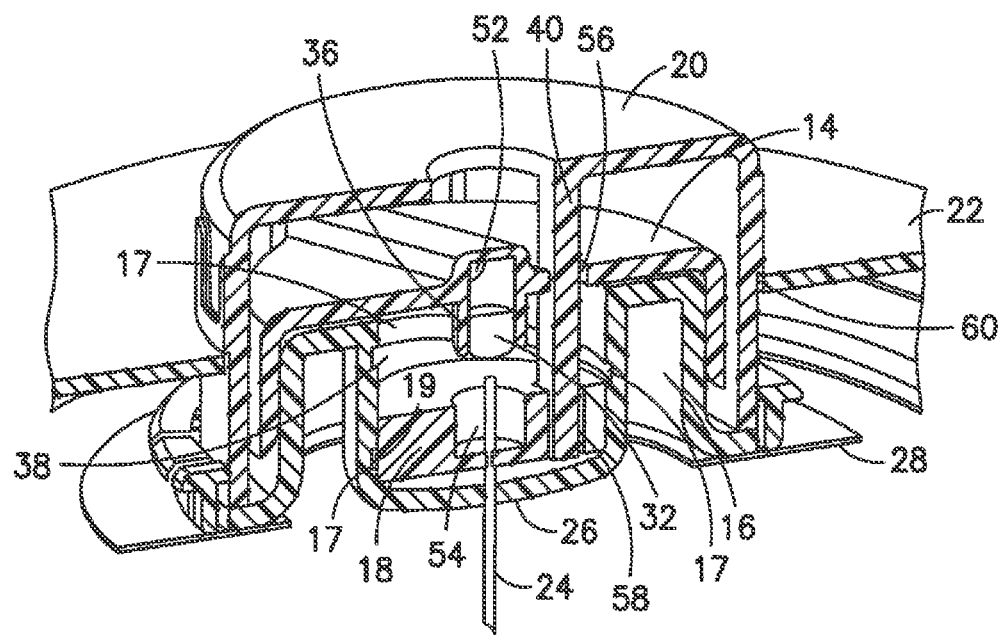
FIG. 3 is a cross-sectional view of the infusion set of FIG. 1 showing the needle in an inserted position, but prior to user retraction, in accordance with an embodiment of the present invention.

FIGS. 1 and 2 are perspective views of an infusion. set in accordance with an embodiment of the present invention. As shown in FIGS. 1-3, the exemplary infusion set 10 can comprise an outer hub 12, main hub 14, main base 16, needle hub 18, and retraction dial 20. An outer ring 22 rotatably extends between the outer hub 12 and retraction dial 20. The hub, base and other elements can be constructed of a molded plastic material, polycarbonate, thermoplastic polymer such as polyethylene terephthalate (PET and PETG), or similar materials.

As shown in greater detail in FIGS. 2 and 3, the needle hub 18 is positioned within the main base 16, and comprises a needle 24. The main base 16 contains the needle hub 18 and an optional needle hub adhesive layer 26. A main base inner adhesive layer 28 can also be provided on the main base 16, and an outer hub adhesive layer 30 can be provided on the outer hub 12.

The needle hub 18 is held within an opening of the main base 16 via a helical threaded engagement between the needle hub 18 and the main base 16. A female thread groove 17 in the wall of opening 38 receives a male thread 19 on the needle hub 18. In doing so, rotation of the needle hub 18 within the opening 38 of the main base 16 serves to advance or retract the needle hub 18 via the threaded engagement, within the opening 38 of the main base 16, thereby advancing or retracting the needle 24 relative to the main base 16 adhered to the skin surface.

Figure 4:
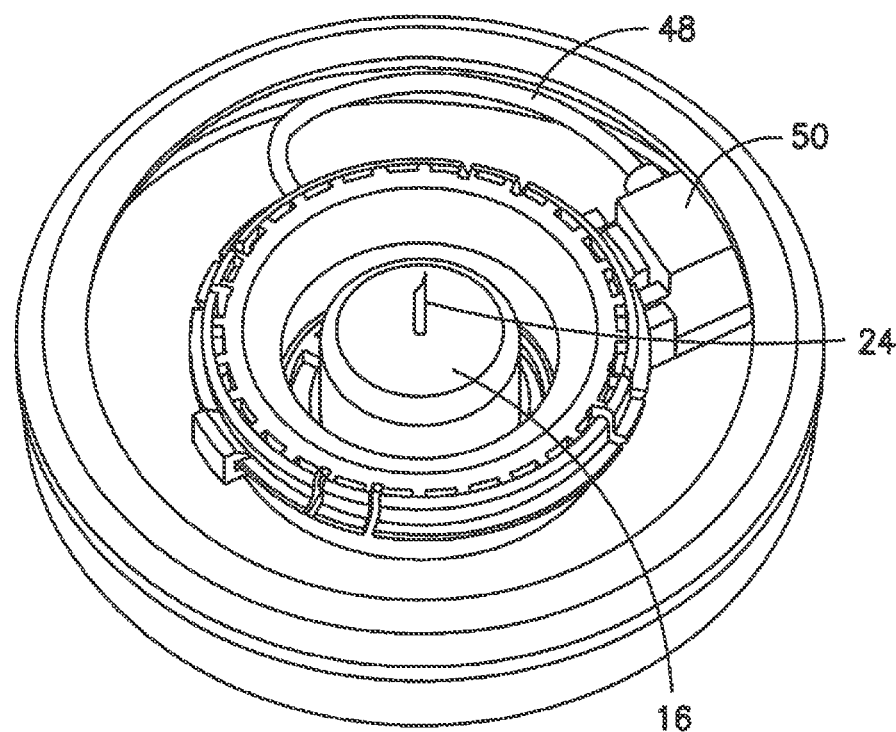
FIG. 4 is a bottom perspective view of the infusion set of FIG. 1 shown without an adhesive layer for illustrative purposes in accordance with an embodiment of the present invention.

The main hub 14 rotatably covers the main base 16 and provides a fluid communication channel 52 between an inner septum 32 and a valve connection septum 34. The main hub 14 is held in place by the flexible tube connection 48 between the main hub 14 and the outer ring 22, as shown in FIG. 4, and by the geometry of the main base 16 and the outer ring 22. As illustrated in FIG. 3, the needle 24 comprises first and second ends, wherein the first end is configured to penetrate a skin surface (not shown), and the second end (which may be sharpened or unsharpened) is configured to penetrate an inner septum 32 (which may be pre-slit and/or pierceable) as described in greater detail below. The inner septum 32 is held within a protrusion 36 of the main hub 14, which is configured to slidably engage a similarly shaped opening 54 in the needle hub 18 as the needle hub is advanced or retracted. The needle 24 can comprise a 31 gauge, 3 mm in length, single-bevel stainless steel needle/cannula, but is not limited thereto. In other embodiments of the present invention, the needle 24 can be plastic or other material, between 27 gauge and 34 gauge, between 2 mm and 5 mm in length, and be provided with a tri-bevel or 5-bevel needle. The needle 24 can be bonded to the needle hub 18 with an adhesive, such as a Loctite/UV cured adhesive, or can be over molded with, or threaded into, the needle hub. Further, other embodiments of the present invention, the needle 24 can be replaced with a soft cannula provided with an internal introducer needle that can be retracted inside the soft cannula. The needle 24 can also comprise a needle longer than that used to simply target the intradermal layer, since the needle of the exemplary embodiments of the present invention is first inserted to a depth of, for example, 5 mm to 6 mm, and then retracted to the targeted intradermal depth of for example, 3 mm or less, As described in greater detail below, this allows use of a longer needle, minimizes the risk of tenting or skin deflection affecting the final insertion depth, and creates an opening to minimize pressure.

The example shown in FIG. 3 illustrates an infusion set wherein the needle 24 has been inserted (or, in the case of a soft cannula and internal introducer needle, wherein the soft cannula and introducer needle have been inserted), and the retraction dial 20 exposed. The retraction dial 20 comprises at least one member 40 extending through an opening 56 of the main hub 14 and terminating in an opening 58 of the needle hub 18 to transmit a rotary force thereto.

The retraction dial 20 is configured to cover the main hub 14 and main base 16 to permit user adjustment of the needle 24 depth. To do so, the retraction dial 20 comprises the least one member 40 extending through the opening 56 of the main hub 14 and terminating in the opening 58 of the needle hub 18. Accordingly, when the retraction dial 20 and member 40 are turned, the main hub 14 and needle hub 18 are turned with the retraction dial 20. However, the main base 16 remains stationary, in adhesive contact with the skin surface. Accordingly, as the needle hub 18 is rotated by the member 40, the threaded engagement with the stationary main base 16 results in an upward or downward movement of the needle hub 18 and the attached needle 24 (or, in the case of a soft cannula and internal introducer needle, results in the introducer needle being retracted or advanced inside the soft cannula).

Accordingly, by turning the retraction dial 20, a user can retract (i.e., move upward) the needle 24. In doing so, a desired depth of needle penetration can be achieved more precisely. Further, the passageway initially created by the fully inserted needle, results in an opening or unfilled passageway as the needle 24 is slightly retracted. The benefits associated with infusion to this additional unfilled passageway are described below. Still further, as the needle 24 is retracted, the second end of the needle 24 contacts and pierces the inner septum 32, such that the needle 24 is in fluid communication with the channel 52 of the main hub 14.

Figure 5:
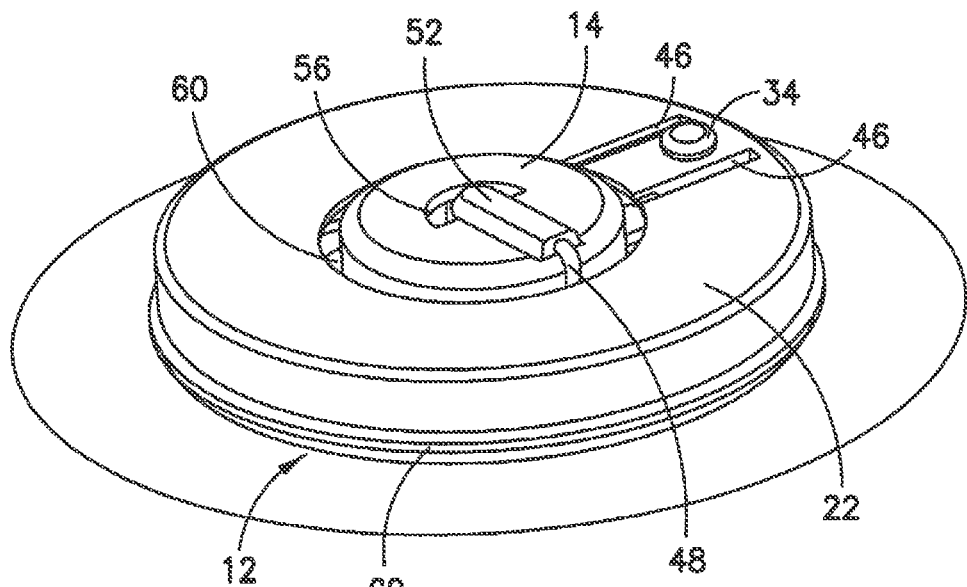
FIG. 5 is a top perspective view of the infusion set of FIG. 1 with the retraction dial removed in accordance with an embodiment of the present invention.

The retraction dial 20 is further configured to simply pull free from the main hub 14 and main base 16 after the desired retraction, as the member 40 is simply held in place by friction engagement with the through-openings 56 and 58, and the opening 60 between the main hub 14 and outer ring 22. Accordingly, upon reaching the desired retraction depth, which can be denoted by a positive stop or some other user-detectable feature, the retraction dial 20 can be removed, thereby leaving the device as shown in FIG. 5. The retraction dial 20 can be marked to denote needle depth, or can be configured to release from the infusion set when the needle reaches a desired depth (i.e. about one rotation or 360 degrees). Still further, it may be desirable to retain the retraction dial 20 in place for later needle height adjustments. By allowing the user to make minute adjustments to the needle height within the intradermal layer, tissue tolerance of infusion may increase. Also, occlusions caused by foreign body response at the end of the needle may be released by these movements. Such a height adjustment feature is easy to adjust in small increments, yet difficult to move accidentally. A release button (not shown) can also be provided. it can also be possible to allow the user to selectively adjust the height to either a subcutaneous or intradermal height setting.

Figure 6:
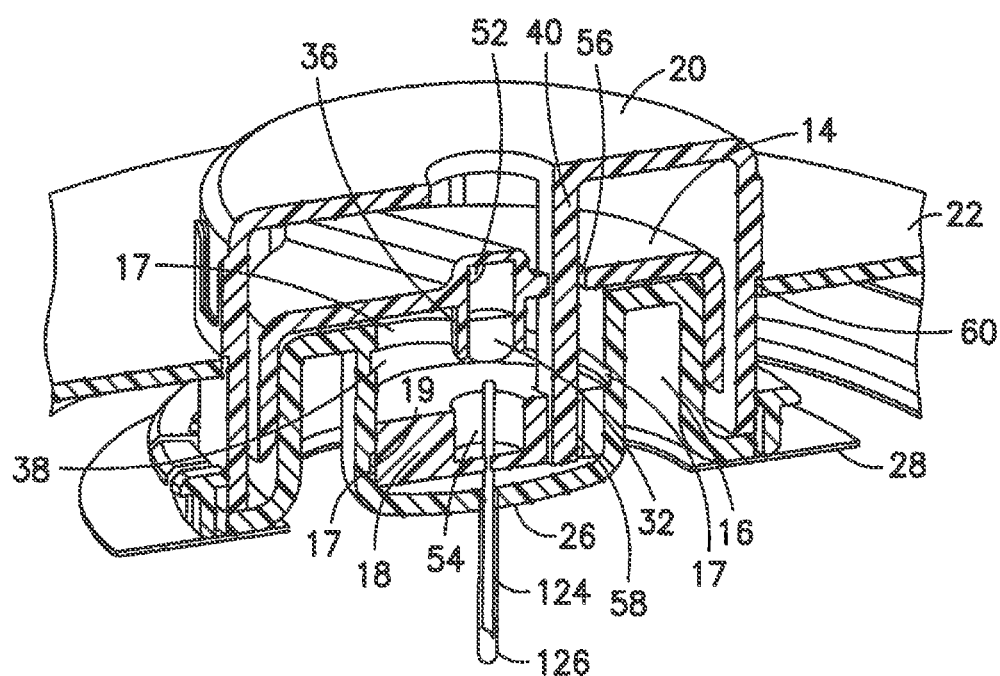
FIG. 6 is a bottom perspective view of the infusion set of FIG. 1 illustrating a soft cannula insertion in accordance with an embodiment of the present invention.

In yet another exemplary embodiment of the present invention shown in FIG. 6, an internal introducer needle 124 can be used to insert a soft cannula 126, and then be partially retracted or withdrawn a distance into the cannula using the retraction dial 20. In this case, the retraction dial 20 can be used to control a distance the introducer needle is withdrawn into the cannula, and subsequently, to control the length of flexible cannula free of the introducer needle. For example, the device can be used to insert the soft cannula 126 and the retraction dial 20 can be used to retract or withdraw the introducer needle 124 some distance back into the soft cannula. The soft cannula can comprise Teflon or Vialon, and be between 25 gauge and 32 gauge. In such an exemplary embodiment, a steel introducer needle can be provided and be between 27 gauge and 34 gauge for proper fitting inside the soft cannula.

Figure 7:
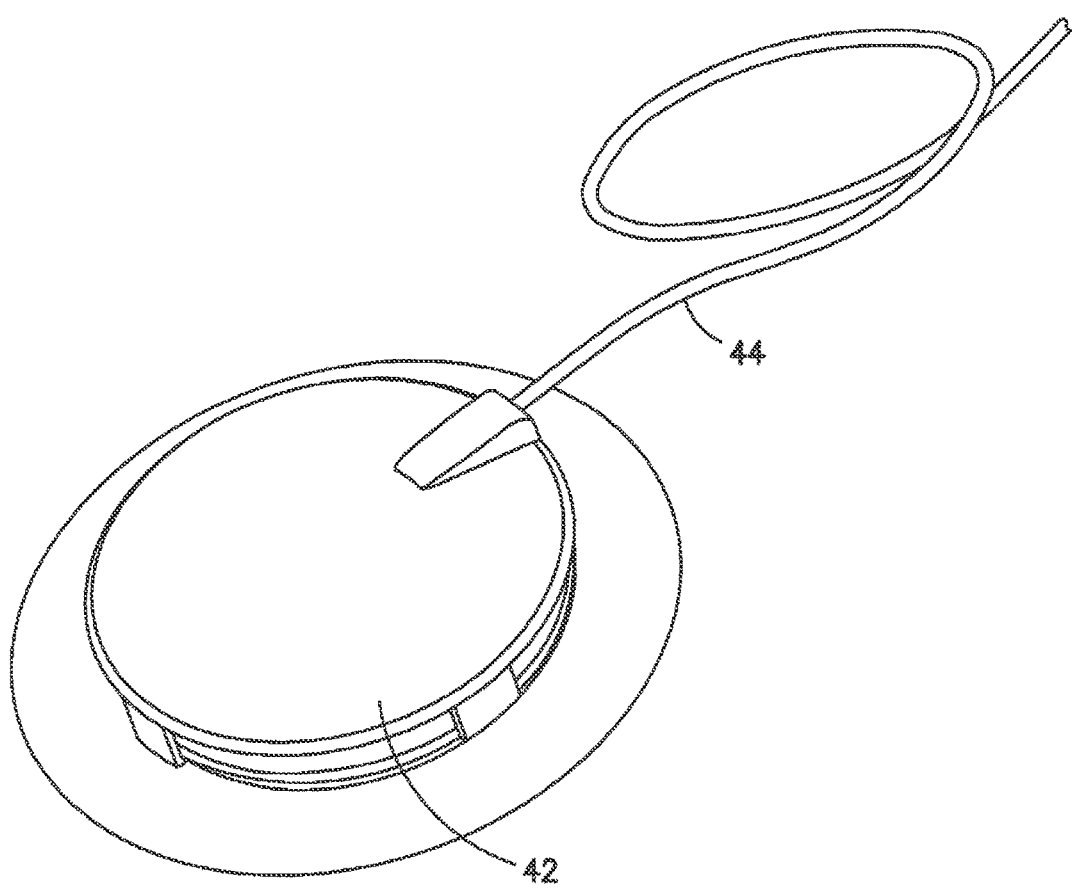
FIG. 7 is a top perspective view of the infusion set of FIG. 1 with the retraction dial removed and the infusion pump tube connection in place in accordance with an embodiment of the present invention.

At this time, the infusion pump tube attachment 42 and tubing 44 to the infusion pump (not shown) can be attached to the top of the infusion set as shown in FIG. 7. FIG. 7 is a top perspective view of the infusion set of FIG. 1 with the retraction dial removed and the infusion pump tube connection in place. The infusion pump tube attachment 42 comprises a circular cover piece to which the tubing 44 is attached and routed through to a septum piercing member (not shown) to engage and pierce the valve connection septum 34. Alignment between the infusion pump tube attachment 42 and the valve connection septum 34 is achieved through the engagement with the self-alignment features, or slots, 46 in the outer ring 22. For example, an inner surface of the cover piece of the infusion pump tube attachment 42 can comprise one or more projections or boss features (not shown) which mate with the slots 46 to thereby allow complete downward assembly of the infusion pump tube attachment 42 with the infusion set when the valve connection septum 34 is in alignment for piercing.

In addition, the infusion pump tube attachment 42 is free to rotate 360 degrees, allowing the tubing 44 to the pump to be arranged in a comfortable orientation. To do so, the outer ring 22 to which the tube attachment 42 is secured, is rotatable between the outer hub 12 and the main hub 14. Specifically, the outer ring 22 of the device is configured to be rotatable along track-like features 62 in the outer hub 12, which is fixed to the user's skin surface. By connecting the outer hub 12 and the outer ring 22 via the track features 62, and connecting the outer ring 22 to the main hub 14 via the thin flexible length of tubing 48, the outer ring 22 and valve connection septum 34 can rotate as permitted by the flexible tubing 48, In doing so, the infusion pump tube attachment 42 is permitted to rotate. In the exemplary embodiment shown, the flexible tubing 48 at least partially encircles the main hub 14 and main base 16, which permits a shorter or flatter device profile.

Vibrational and shock isolation of the main hub 14 and main base 16, from the outer hub 12, outer ring 22 and valve connection septum 34, is achieved in a number of ways, including the provision of the track features 62 between the outer hub 12 and the outer ring 22, and the flexible tubing 48 between the fluid channel 52 of the main hub 14 and connection valve 50 of the outer ring 22. Further, once the retraction dial 20 is removed, the main hub 14 and main base 16 are separated from the outer hub 12 and outer ring 22. That is, first, the main hub 14 and the outer ring 22 are physically separated and are connected only by the flexible tubing 48, and second, the main hub 14 and main base 16 are secured to the skin surface via adhesive layers 26 and 28, and the outer hub 12 is secured to the skin surface via adhesive layer 30, wherein the layers 26, 28 and 30 are physically separated. In doing so, the only connection between the main hub 14 and main base 16, and the outer hub 12 and outer ring 22 (and the attached infusion pump tube attachment 42), is the flexible tubing 48. Further, once covered by the tube attachment described in greater detail below, external contact with the main hub 14 and main base 16 is prevented.

The exemplary embodiments of the present invention provide a novel means of delivering insulin to the intradermal layers of skin via standard insulin pumps, but are not limited thereto. The invention can also be applied to patch pumps or other infusion devices.

Further, the exemplary embodiments comprise a straight microneedle, needle, or other cannula, that can be inserted by the user into the deeper dermis or the subcutaneous layers of the skin, and can then be withdrawn with a great deal of precision into the dermal layer, where it is held by adhesive and/or mechanical preload.

Initial insertion of the infusion set with a user controllable needle depth is similar to the operation of fixed steel cannula devices currently on the market. The user first peels off a flexible backing, removes a needle cover, and then inserts the needle into the infusion site. After ensuring good skin adhesion, the user then turns the retraction dial. The retraction dial can be marked to denote needle depth, reach a positive stop, or can be configured to release from the infusion set when the needle reaches a desired depth (i.e. about one rotation or 360 degrees). In an exemplary embodiment, the retraction dial is configured to turn a quarter turn (i.e., 90 degrees) to reach the desired depth. The user can then remove the retraction dial and attach the pump tube attachment, in the case of an infusion set, from the top of the device. The device is then ready to prime and deliver insulin. In addition, the valve connection is free to rotate up to 360 degrees, allowing the tubing to the pump to be arranged in a comfortable orientation.

As the retraction dial 20 turns, the needle 24 and needle-hub 18 of the device move up the threaded engagement 17 and 19 located in the main base 16. The needle 24 protrudes from both sides of the needle hub 18 and, on the side opposite the side that pierces the skin, the needle 24 pierces through the inner septum 32 as it moves upward, establishing fluid communication with the valve connection interface. As the needle 24 pierces the inner septum 32 in such a manner, it can be locked in place with respect to the main base 16. To do so, a detent or projection not shown) can be provided on an outer surface of the needle hub 18 that is configured to mate with a similar detent or projection (not shown) provided on an inner surface of the main base 16 when the needle hub 18 reaches the desired position. Once engaged, the detents can lock the needle hub 18 in place with the main base 16. The fluid path 30 is open through the main hub 14 and the flexible piece of tubing 48 which leads to the valve connection septum 34 located in the outer ring 22, which is able to rotate about the main hub 14 and main base 16 as permitted by the track in the outer hub 12 and tubing 48.

As shown in FIG. 3, the main base 16 also provides a contour on a lower surface that contacts the skin surface around the needle 24, providing a slight preload, or indentation, on the skin surface which helps maintain the needle position within the intradermal layer. In addition, adhesive layer 26 can be placed on the main base 16 in the vicinity of the needle 24 to help with the anchoring of the needle in the skin surface.

The outer ring 22 of the device is configured to be rotatable along the track-like features 62 in the outer hub 12, which is fixed to the user's skin surface. By connecting the outer hub 12 and the outer ring 22, to the main hub 14 and main base 16, via the thin flexible length of tubing 48, external forces and vibrations are absorbed by the outer hub 12 and the outer ring 22, but not by the main hub 14, main base 16, needle hub 18 and the needle 24. Finally, the infusion pump tube attachment 42 can be attached to the outer ring 22, covering the assembly and providing further isolation of the needle, and the self-centering features of slots 46 ensure that the valve connection needle (not shown) pierces the valve connection septum 34.

As noted above, the passageway initially created by the fully inserted needle, results in an opening or unfilled passageway as the needle 24 is slightly retracted. As known in the art, high pumping pressure (i.e., 20-50 or more psi), can occur during intradermal infusion. However, by first providing the deeper insertion tunnel established by the initial insertion depth as recited above, and the subsequent withdrawal to the infradermal layer, embodiments of the present invention can relieve such pressures by increasing the surface area of the deposition area.

Further, by infusing into the intradermal layer of the skin, the exemplary embodiments of the present invention offer the potential for better absorption of insulin when compared to subcutaneous delivery systems. In doing so, it may be possible for the typical user to both consume less insulin and maintain a better medicament regime.

Other intradermal infusion set concepts are at risk of "tenting", which is the undesired effect where skin is deflected at needle insertion before or during insertion, creating a shape similar to a tent. In doing so, the skin surface tents during needle insertion rather than needle penetration into the skin. However, since a longer needle can be used, and then slightly retracted in the exemplary embodiments of the present invention, the risk of tenting or skin deflection otherwise affecting final insertion depth is reduced. Still further, a small intradermal needle placed perpendicular to the skin and isolated from outside forces causes less pain to the user during use.

In current steel cannula, infusion sets which deliver to the subcutaneous layer, the needle is not isolated from any undesired outside forces which may cause pain when translated to the needle and the needle moves within the skin. Also, other intradermal devices face problems of premature or otherwise undesired needle removal when the device is bumped, if the needle is not isolated from the outside forces.

In the exemplary embodiments of the present invention, the intradermal needle is isolated from outside forces by a cover design, a double ring feature, and the provision of flexible tubing. Such features help to effectively isolate the needle from the outside forces and other interferences.

By infusing into the intradermal layer of the skin, the exemplary embodiments of the present invention offer the potential for better absorption of the insulin when compared to subcutaneous delivery systems. It may be possible for the user to maintain a better medicament regimen while using less insulin. Further, the provision of a small intradermal needle placed perpendicular to the skin and isolated from outside forces causes less pain and discomfort to the user during use.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

What is claimed is:

1. A method for targeting a desired depth to deliver content to an upper skin layer, comprising the steps of:
    placing an infusion set upon an infusion site such that an infusion needle is inserted, said infusion needle forming a part of a content delivery path;
    subsequent to said infusion needle being inserted, retracting said infusion needle until a desired infusion depth of a distal most portion of said content delivery path within said skin is reached; and
    connecting an infusion pump to said infusion set.

2. A method for targeting a desired depth as claimed in claim 1, further comprising delivering medicament through said infusion needle.

3. A method for targeting a desired depth to deliver content to an upper skin layer, comprising the steps of:
    placing an infusion set upon an infusion site such that an infusion needle is inserted;
    turning a retraction dial, releasably coupled with said infusion set, to move said infusion needle until a desired infusion depth within said skin is reached;
    attaching an infusion pump tube attachment to said infusion set; and
    wherein said retraction dial is configured to rotate relative to said infusion set and wherein said rotation is translated into movement of said infusion needle.

4. A method for targeting a desired depth as claimed in claim 3, wherein said rotation of said retraction dial is translated into vertical movement of said infusion needle.

5. A method for targeting a desired depth as claimed in claim 3, further comprising the step of removing said retraction dial from said infusion set.

6. A method to retract an introducer needle some distance into a soft cannula after insertion, comprising the steps of:
    placing an infusion set upon an infusion site such that an introducer needle and soft cannula are inserted;
    turning a retraction dial, releasably coupled with said infusion set, to move said introducer needle until said introducer needle is retracted a desired distance into said soft cannula; and
    connecting an infusion pump to said infusion set to create a fluid path from said infusion pump through said introducer needle and said soft cannula;
    wherein said retraction dial is configured to rotate relative to said infusion set and wherein said rotation is translated into movement of said introducer needle.

7. A method to retract an introducer needle as claimed in claim 6, wherein said rotation of said retraction dial is translated into vertical movement of said introducer needle.

8. A method to retract an introducer needle as claimed in claim 6, further comprising the step of removing said retraction dial from said infusion set.

9. A method for targeting a desired depth to deliver content to an upper skin layer at a reduced pressure, comprising the steps of:
    placing an infusion set upon an infusion site such that an infusion needle is inserted to create an opening in said skin, said infusion needle forming a part of a content delivery path;
    moving said infusion needle so that a distal most portion of said content delivery path is moved to a position within said skin to remove said infusion needle from a portion of said opening; and
    connecting an infusion pump to said infusion set and delivering content to at least said portion of said opening through said infusion needle, wherein said portion of said opening increases a surface area of a deposition area of said skin.

10. A method for targeting a desired depth to deliver content to an upper skin layer at a reduced pressure, comprising the steps of:
    placing an infusion set upon an infusion site such that an infusion needle is inserted to create an opening in said skin;
    turning a retraction dial, releasably coupled with said infusion set, to move said infusion needle to remove said infusion needle from a portion of said opening;
    attaching an infusion pump tube attachment to said infusion set and delivering content to at least said portion of said opening through said infusion needle, wherein said portion of said opening increases a surface area of a deposition area of said skin; and
    wherein said retraction dial is configured to rotate relative to said infusion set and wherein said rotation is translated into movement of said introducer needle.

11. A method for targeting a desired depth to deliver content as claimed in claim 10, wherein said rotation of said retraction dial is translated into vertical movement of said introducer needle.

12. A method for targeting a desired depth to deliver content as claimed in claim 10, further comprising the step of removing said retraction dial from said infusion set.

* * * * *